(12) United States Patent
Park et al.

(10) Patent No.: US 11,826,155 B2
(45) Date of Patent: Nov. 28, 2023

(54) TRANSPARENT FLEXIBLE BIO-ELECTRODE AND METHOD FOR MANUFACTURING SAME

(71) Applicant: University of Seoul Industry Cooperation Foundation, Seoul (KR)

(72) Inventors: Dong-Wook Park, Seongnam-si (KR); Dongjun Han, Seoul (KR)

( * ) Notice: Subject to any disclaimer, the term of this patent is extended or adjusted under 35 U.S.C. 154(b) by 797 days.

(21) Appl. No.: 16/858,965

(22) Filed: Apr. 27, 2020

(65) Prior Publication Data

US 2021/0244304 A1 Aug. 12, 2021

(30) Foreign Application Priority Data

Feb. 10, 2020 (KR) .................. 10-2020-0015499

(51) Int. Cl.
| | |
|---|---|
| *A61B 5/283* | (2021.01) |
| *A61B 5/369* | (2021.01) |
| *C09D 181/02* | (2006.01) |
| *C09D 125/18* | (2006.01) |
| *G03F 7/16* | (2006.01) |
| *H01B 13/00* | (2006.01) |
| *H01B 1/12* | (2006.01) |

(52) U.S. Cl.
CPC .............. *A61B 5/369* (2021.01); *A61B 5/283* (2021.01); *C09D 125/18* (2013.01); *C09D 181/02* (2013.01); *G03F 7/16* (2013.01); *H01B 1/124* (2013.01); *H01B 13/0036* (2013.01); *A61B 2562/0215* (2017.08); *A61B 2562/125* (2013.01); *A61B 2562/164* (2013.01); *A61B 2562/227* (2013.01)

(58) Field of Classification Search
CPC ....... A61B 5/24; A61B 5/25262; A61B 5/293; A61B 5/294; A61B 5/37; A61B 5/6848; A61B 5/685; A61B 5/6868
See application file for complete search history.

(56) References Cited

U.S. PATENT DOCUMENTS

| | | | |
|---|---|---|---|
| 10,736,250 B1* | 8/2020 | Kim ..................... | H05K 9/0096 |
| 2011/0156577 A1* | 6/2011 | Koyama ............... | H10K 50/85 |
| | | | 313/504 |
| 2012/0168682 A1* | 7/2012 | Kim ....................... | H01B 1/127 |
| | | | 252/500 |
| 2014/0067023 A1 | 3/2014 | Register | |
| 2019/0022375 A1* | 1/2019 | Cruttenden .............. | A61B 5/24 |
| 2022/0066582 A1* | 3/2022 | Park ....................... | H01B 3/448 |

FOREIGN PATENT DOCUMENTS

| | | | | |
|---|---|---|---|---|
| CN | 108832002 B | * | 4/2022 | ......... H01L 51/0003 |
| KR | 10-2015-0027336 A | | 3/2015 | |
| KR | 1020190076079 A | | 7/2019 | |
| KR | 20190101208 A | * | 8/2019 | ............... H01B 5/00 |

OTHER PUBLICATIONS

KR OA dated Jul. 28, 2022.
KR OA dated Jan. 28, 2022.

* cited by examiner

*Primary Examiner* — Eun Hwa Kim
(74) *Attorney, Agent, or Firm* — Harvest IP Law, LLP

(57) ABSTRACT

A transparent flexible bio-electrode and a method for manufacturing the same are provided. The transparent flexible bio-electrode includes a substrate, electrode sites disposed at one side on the substrate, electroconductive contacts disposed at the other side on the substrate, and an interconnector configured to connect the electrode sites and the contacts.

11 Claims, 8 Drawing Sheets

TRANSPARENT FLEXIBLE BIO-ELECTRODE AND METHOD FOR MANUFACTURING SAME

CROSS-REFERENCE TO RELATED APPLICATION

This application claims priority to Korean Patent Application No. 10-2020-0015499, filed on Feb. 10, 2020, the disclosure of which is incorporated by reference herein in its entirety.

BACKGROUND

1. Field

Apparatuses and methods consistent with exemplary embodiments relate to a transparent flexible bio-electrode and a method for manufacturing the same and, more particularly, to a transparent flexible bio-electrode operating as a single sensor which is not an electrode for supplying electric power to a semiconductor element and also using as an in vivo bio-sensor based on biocompatible properties.

2. Description of the Related Art

Treatment using an electrical stimulation of the brain has been expanded to treat a neurological disorders such as Parkinson's disease, epilepsy, Tourette syndrome (e.g., tic disorder), or the like. In particular, deep brain stimulation (DBS), which stimulates deep brain regions to alleviate symptoms of neurological disorders, has become an effective surgical therapy for patients who have difficulty relieving symptoms. Hundreds of deep brain stimulation surgeries have been performed annually at about 20 medical centers in Korea, and the utilization of the deep brain stimulation has increased worldwide.

A deep brain stimulation electrode (hereinafter referred to as 'DBS electrode') is various types of neural electrodes. Deep brain stimulation provides periodic electric stimulation to the DBS electrode by injecting the DBS electrode into the deep brain, helping to activate dopamine neurons. An application of these electric stimulation has expanded to include treatments for Alzheimer's disease, obesity and addiction as well as Parkinson's disease, hand tremor (e.g., essential tremor), depression, and epilepsy, and an active research on the electric stimulation has recently been conducted.

However, as conventional DBS electrode is formed of an opaque metal such as tungsten or platinum, the DBS electrode causes image distortion in medical images such as magnetic resonance imaging (MRI) and the like. Distorted image information may obstruct exact positioning of the DBS electrode during operation, or accurate diagnosis of other neurological disorders after electrode transplantation.

An image distortion occurs in MRI because magnetic susceptibility of a metallic material is substantially greater than that of biological tissue and in vivo moisture ($H_2O$). Therefore, an electrode using carbon fibers having a relatively less magnetic susceptibility has been suggested. However, there has been a limit to the decrease in MRI image distortion due to a large amount of carbon atoms within the carbon fibers. Further, the carbon fibers have a potential risk that electrical connections may be cut when the carbon fibers are transplanted in vivo for a long period due to a weak mechanical strength of the carbon fibers.

SUMMARY

Aspects of one or more exemplary embodiments provide a transparent flexible bio-electrode which is transparent and flexible, which is formed of biocompatible materials such that the transparent flexible bio-electrode has biocompatibility, and which is excellent in brainwave detection performance by having excellent electrical performance and high surface-to-volume ratio.

Aspects of one or more exemplary embodiments also provide a transparent flexible bio-electrode capable of applying to optogenetics for analyzing brain by using light, and capable of using in medical images photographed for the purpose of diagnosis after an electrode inserting operation. Specifically, the transparent flexible bio-electrode may be applied to a neural electrode (e.g., electrocorticography (ECoG), electroencephalography (EEG), or penetrating electrode) for measuring brainwaves, that is, electric signals generated from the brain, an electromyogram sensor for measuring electromyogram signals generated from muscles, electroretinogram (ERG) and artificial retina.

Aspects of one or more exemplary embodiments also provide a method for manufacturing a transparent flexible bio-electrode, the method which can manufacture a large quantity of a microscale microelectrode to a large area on a wafer by using a solution process, and which can reduce costs by improving productivity and adjusting consumption of material.

According to an aspect of an exemplary embodiment, there is provided a transparent flexible bio-electrode including: a substrate, electrode sites disposed at one side on the substrate, electroconductive contacts disposed at the other side on the substrate, and an interconnector configured to connect the electrode sites and the contacts.

The electrode sites may include a metal nanowire layer disposed on the substrate and a conductive polymer layer disposed on the metal nanowire layer.

The conductive polymer layer may have irregularities depending on whether a metal nanowire exists under the conductive polymer layer.

A ratio (ratio 2/ratio 1) of a surface area to a volume may be 1.5 to 2.0, the ratio 2 being a ratio of a surface area to a volume when the metal nanowire layer is formed on the substrate and the conductive polymer layer is formed on the metal nanowire layer, and the ratio 1 being a ratio of a surface area to a volume when only the conductive polymer layer is formed on the substrate.

A thickness of the electrode sites may be about 100 to 173 nm.

The conductive polymer layer may have a thickness thinner than that of the metal nanowire layer.

A diameter of the metal nanowire may be 20 to 40 nm, and a thickness of the conductive polymer layer may be 90 to 200 nm.

The conductive polymer may be one selected from the group consisting of poly (3, 4-ethylenedioxythiophene) (PEDOT), poly (styrenesulfonate) (PSS), poly (3-hexylthiophene) (P3HT), poly (3-octylthiophene) (P3OT), poly (p-phenylene vinylene) (PPV), poly (9, 9-dioctylfluorene), poly (2-methoxy-5-(2'-ethyl-hexyloxy)-1, 4-phenylene vinylene) (MEH-PPV), poly (2-methoxy-5-(3', 7'-dimethyl-octyloxy)-1, 4-phenylenevinylene) (MDMO-PPV), derivatives thereof, and mixtures thereof.

The conductive polymer may be doped with a first dopant selected from the group consisting of dimethyl sulfoxide (DMSO), ethylene glycol (EG), sorbitol and mixtures thereof, and a second dopant selected from the group consisting of 3-glycidyloxypropyl trimethoxysilane (GOPS), polyvinylpyrrolidone (PVP), polyvinyl alcohol (PVA), and mixtures thereof.

The metal nanowire may be a nanowire of a metal selected from the group consisting of silver, nickel, copper, aluminum, gold, and alloys thereof.

The transparent flexible bio-electrode may further include an overlayer comprising a cyclic olefin polymer represented by following Chemical Formula 1 on the electrode sites and the electroconductive contacts,

[Chemical Formula 1]

where, X and Y are each independently a substituent selected from the group consisting of a hydrogen group, an alkyl group, an alkoxy group, an alkylether group, an aryl group, and combinations thereof, and n is a number of repeating units.

The overlayer may include opening parts such that the electrode sites and the electroconductive contacts are exposed and connected to an external device.

A thickness of the overlayer may be 50 μm or less.
A thickness of the substrate may be 50 μm or less.

According to an aspect of another exemplary embodiment, there is provided a method for manufacturing a transparent flexible bio-electrode, the method including: forming a metal pattern layer comprising electroconductive contacts an electroconductive interconnector on a substrate; coating a metal nanowire layer on the substrate such that the metal nanowire layer comes into contact with the metal pattern layer; and coating a conductive polymer layer on the metal nanowire layer.

The method for manufacturing a transparent flexible bio-electrode may further including: patterning the metal nanowire layer and the conductive polymer layer; and coating an overlayer comprising a cyclic olefin polymer represented by following Chemical Formula 1 on the substrate including the metal nanowire layer and conductive polymer layer,

[Chemical Formula 1]

where, X and Y are each independently a substituent selected from the group consisting of a hydrogen group, an alkyl group, an alkoxy group, an alkylether group, an aryl group, and combinations thereof, and n is a number of repeating units.

The conductive polymer may be one selected from the group consisting of poly (3, 4-ethylenedioxythiophene) (PEDOT), poly (styrenesulfonate) (PSS), poly (3-hexylthiophene) (P3HT), poly (3-octylthiophene) (P3OT), poly (p-phenylene vinylene) (PPV), poly (9, 9-dioctylfluorene), poly (2-methoxy-5-(2'-ethyl-hexyloxy)-1, 4-phenylene vinylene) (MEH-PPV), poly (2-methoxy-5-(3', 7'-dimethyl-octyloxy)-1, 4-phenylenevinylene) (MDMO-PPV), derivatives thereof, and mixtures thereof.

The metal nanowire may be a nanowire of a metal selected from the group consisting of silver, nickel, copper, aluminum, gold, and alloys thereof.

BRIEF DESCRIPTION OF THE DRAWINGS

The above and other aspects will be more apparent from the following description of the exemplary embodiments with reference to the accompanying drawings, in which.

DETAILED DESCRIPTION

Various modifications may be made to the embodiments of the disclosure, and there may be various types of embodiments. Thus, specific embodiments will be illustrated in drawings, and the embodiments will be described in detail in the description. However, it should be noted that the various embodiments are not for limiting the scope of the disclosure to a specific embodiment, but they should be interpreted to include all modifications, equivalents or alternatives of the embodiments included in the ideas and the technical scopes disclosed herein. Meanwhile, in case it is determined that in describing the embodiments, detailed explanation of related known technologies may unnecessarily confuse the gist of the disclosure, the detailed explanation will be omitted.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "including" be understood to imply the inclusion of stated elements but not the exclusion of any other elements.

In an exemplary embodiment, "a module," "a unit," or "a part" performs at least one function or operation, and may be realized as hardware, such as a processor or integrated circuit, software that is executed by a processor, or a combination thereof. In addition, a plurality of "modules," a plurality of "units," or a plurality of "parts" may be integrated into at least one module or chip and may be realized as at least one processor except for "modules," "units" or "parts" that should be realized in a specific hardware.

Unless otherwise defined, an alkyl group includes a primary alkyl group, a secondary alkyl group, and a tertiary alkyl group.

Unless otherwise defined, a halogen group means a fluoro group, a chloro group, a bromo group, or an iodo group.

Unless otherwise defined, all compounds or substituents may be substituted or unsubstituted compounds or substituents. Here, 'substituted' means that hydrogen is substituted for one selected from the group consisting of a halogen group, a hydroxy group, a carboxy group, a cyano group, a nitro group, an amino group, a thio group, a methylthio group, an alkoxy group, a nitrile group, an aldehyde group, an epoxy group, an ether group, an ester group, a carbonyl group, an acetal group, a ketone group, an alkyl group, a perfluoroalkyl group, a cycloalkyl group, a heterocycloalkyl group, a benzyl group, an aryl group, a heteroaryl group, derivatives thereof, and combinations thereof.

Unless otherwise defined, the alkyl group means a linear or branched $C_1$-$C_{10}$ alkyl group, a halogenated alkyl group means a linear or branched $C_1$-$C_{10}$ halogenated alkyl group, an aryl group means a $C_6$-$C_{30}$ aryl group, a heteroaryl group means a $C_2$-$C_{30}$ heteroaryl group, and an alkoxy group means a $C_1$-$C_{10}$ alkoxy group.

Unless otherwise defined, the halogenated alkyl group means an alkyl group in which some or all hydrogen atoms are substituted for halogen atoms. For example, the halogenated alkyl group may include a perfluoro alkyl group.

Unless otherwise defined, the aryl group means a chemical group obtained by removing a hydrogen atom from a $C_2$-$C_{30}$ monocyclic or polycyclic compound comprising one or more benzene rings, and derivatives thereof. For example, a monocyclic or polycyclic compound comprising a benzene ring may include: a benzene ring; toluene, xylene or the like in which an alkyl side chain is attached to the benzene ring; biphenyl or the like to which two or more benzene rings are linked via a single bond; fluorene, xanthene, anthraquinone or the like in which a benzene ring is fused to a cycloalkyl group or a heterocycloalkyl group; and naphthalene, anthracene or the like in which two or more benzene rings are fused to each other.

Unless otherwise defined, a prefix 'hetero' means that one to three heteroatoms selected from the group consisting of —N—, —O—, —S— and —P— substitute carbon atom. For example, a compound comprising a nitrogen atom as a heteroatom may include pyridine, pyrrole, carbazole, etc., and a compound comprising an oxygen atom as a heteroatom may include furan, dibenzofuran, dibenzothiophene, diphenylamine, etc.

Hereinbelow, exemplary embodiments will be described with reference to the accompanying drawings. In order to clearly illustrate the disclosure in the drawings, some of the elements that are not essential to the complete understanding of the disclosure may be omitted, and like reference numerals refer to like elements throughout the specification.

Figure 1:
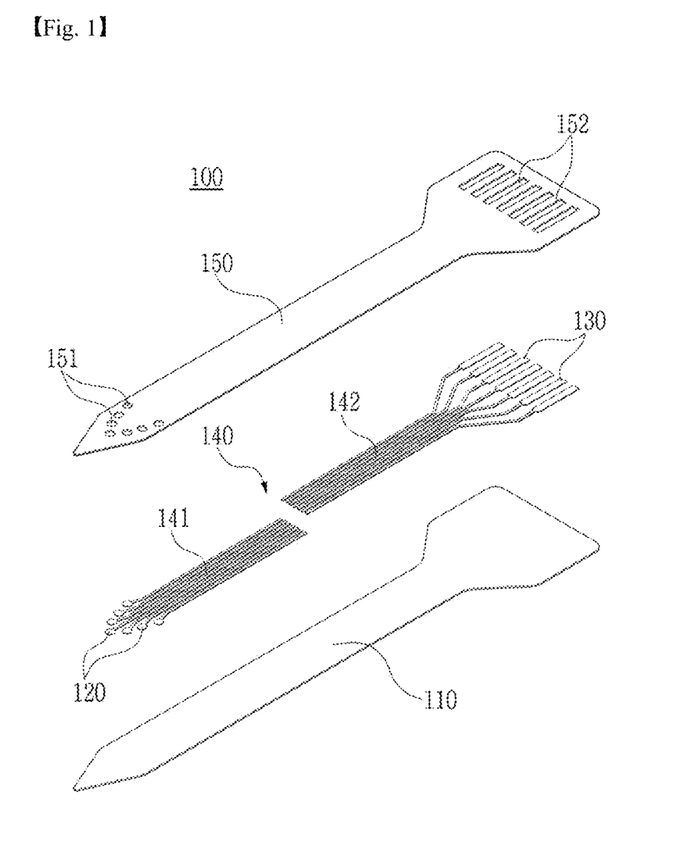
FIG. 1 is an exploded perspective view showing a transparent flexible bio-electrode according to an exemplary embodiment.

FIG. 1 is an exploded perspective view showing a transparent flexible bio-electrode according to an exemplary embodiment. Referring to FIG. 1, a transparent flexible bio-electrode 100 may include a substrate 110, a plurality of electrode sites 120 disposed at one side on the substrate 110, a plurality of electroconductive contacts 130 disposed at the other side on the substrate 110, and an electroconductive interconnector 140 connecting the electrode sites 120 and the electroconductive contacts 130.

Figure 2:
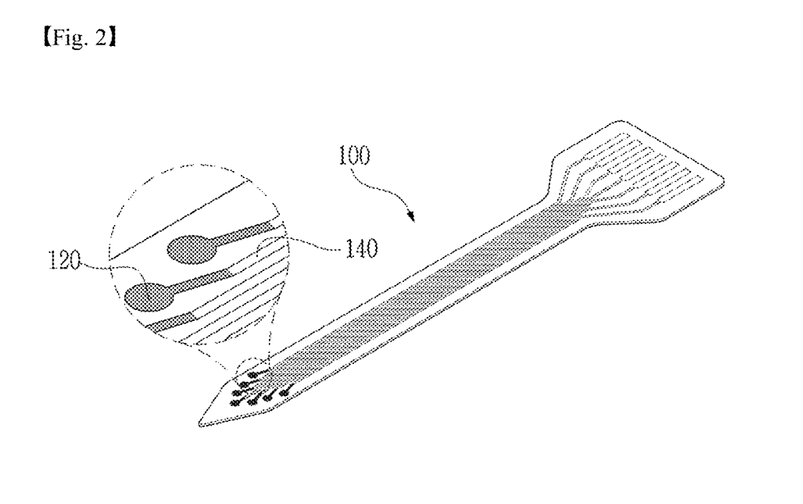
FIG. 2 is an enlarged view illustrating an enlarged connection part between electrode sites and an interconnector of FIG. 1.
Figure 3:
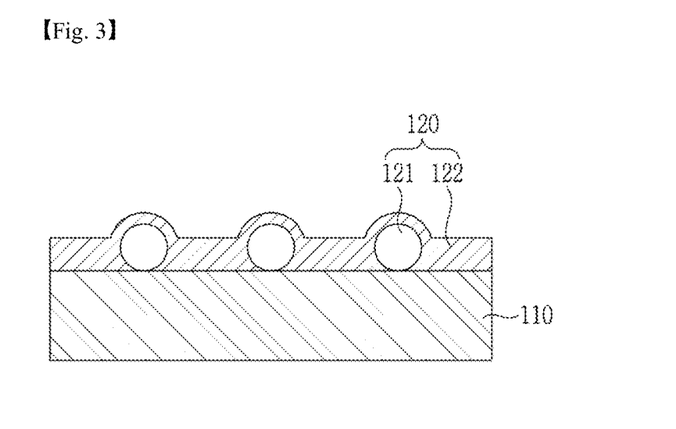
FIG. 3 is a cross-sectional view schematically showing a cross section of electrode sites according to an exemplary embodiment.

FIG. 2 illustrates an enlarged connection part obtained by enlarging a connection part between the electrode sites 120 and the interconnector 140 of FIG. 1, and FIG. 3 is a cross-sectional view schematically showing a cross section of electrode sites 120.

Referring to FIG. 3, the transparent flexible bio-electrode 100 may include a metal nanowire layer 121 disposed on the substrate 110, and a conductive polymer layer 122 disposed on the metal nanowire layer 121.

The conductive polymer layer 122 may cover the metal nanowire layer 121 and fill an empty space between random networks between metal nanowires. Therefore, an electroconductive current path is formed in a region which is metal nanowire random network-free or has a very low density by using the conductive polymer layer 122.

Because the conductive polymer layer 122 allows the electroconductive current path to be formed with respect to a portion in which a random network of a metal nanowire is cut after bending, the conductive polymer layer 122 may be more flexible and have a higher electroconductivity than when the metal nanowire is used alone.

Further, due to existence of a metal nanowire having more excellent conductivity than the conductive polymer layer 122, a thickness of the conductive polymer layer 122 can be reduced on the same resistance basis. Accordingly, more transparent characteristics can be obtained.

In addition, the conductive polymer layer 122 which has already verified biocompatibility can secure stability in a region that has come into contact with the human body by surrounding the metal nanowire layer 121.

Because the metal nanowire layer 121 formed of random networks between metal nanowires is not flat, the conductive polymer layer 122 has irregularities according to whether a metal nanowire exists in a lower part of the conductive polymer layer 122 as illustrated in FIG. 3. In other words, a concave part is formed in a region of the conductive polymer layer 122 in which the metal nanowire does not exist in the lower part of the conductive polymer layer 122 as the conductive polymer layer 122 comes into contact with the substrate 110, while a convex part as large as a diameter of the metal nanowire is formed in a region of the conductive polymer layer 122 in which the metal nanowire exists in the lower part of the conductive polymer layer 122.

As a surface area of the transparent flexible bio-electrode 100 that comes into contact with the human body is increased compared to the same area due to surface roughness of the conductive polymer layer 122 generated by a metal nanowire, the transparent flexible bio-electrode 100 is excellent in brainwave detection performance.

For example, if a ratio 2 is a ratio of a surface area to a volume when the metal nanowire layer 121 is formed on the substrate 110 and the conductive polymer layer 122 is formed on the metal nanowire layer 121, and a ratio 1 is a ratio of a surface area to a volume when only the conductive polymer layer 122 is formed on the substrate 110, a ratio (ratio 2/ratio 1) of a surface area to a volume may be 1.5 to 2.0. Specifically, the ratio (ratio 2/ratio 1) may be 1.5 to 1.7. The surface area or volume of the conductive polymer layer 122 may be area of the entire surface area of an independent conductive polymer layer 122. Here, the independent conductive polymer layer 122 is surface area or volume of a single pattern when the conductive polymer layer 122 is patterned. The surface area can be calculated by means of an area of the substrate 110 during manufacturing of samples, and the volume can be calculated by volume including the thickness of an average roughness value measured through an atomic force microscopy (AFM) equipment. A ratio of a surface area to a volume may be obtained by dividing the surface area (in unit: $nm^2$) by the volume (in unit: $nm^3$).

The electrode sites 120 may have a thickness of 100 to 173 nm, and a surface roughness of the conductive polymer layer 122 may be 20 to 68 nm. The surface roughness of the conductive polymer layer 122 can be obtained by calculating a distance between the highest point height and the lowest point height of the conductive polymer layer 122 using the AFM equipment.

The metal nanowire layer 121 may have a diameter of 20 to 40 nm, and specifically 20 to 30 nm. The conductive polymer layer 122 may have a thickness of 90 to 200 nm, and specifically 90 to 120 nm. It is preferable that the conductive polymer layer 122 has a thickness thinner than that of a metal nanowire random network. In this case, the conductive polymer layer 122 may have irregularities according to whether a metal nanowire exists in a lower part of the conductive polymer layer 122, and more transparent characteristics may be obtained as the thickness of the conductive polymer layer 122 decreases.

The conductive polymer layer 122 comprises a conductive polymer. Although any conductive polymers may be used without limitation if the conductive polymers have biocompatibility and electroconductivity, it is preferable to use conductive polymers which are suitable for a flexible element, are resistant to a large number of bending, and are transparent to about 90% of a thickness of about 100 nm.

For example, the conductive polymer may be one selected from the group consisting of poly (3, 4-ethylenedioxythiophene) (PEDOT), poly (styrenesulfonate) (PSS), poly (3-hexylthiophene) (P3HT), poly (3-octylthiophene) (P3OT), poly (p-phenylene vinylene) (PPV), poly (9, 9-dioctylfluorene), poly (2-methoxy-5-(2'-ethyl-hexyloxy)-1, 4-phenylene vinylene) (MEH-PPV), poly (2-methoxy-5-(3', 7'-dimethyloctyloxy)-1, 4-phenylenevinylene) (MDMO-PPV), derivatives thereof, and mixtures thereof. Specifically, the conductive polymer may include a mixture of poly (3, 4-ethylenedioxythiophene) and poly (styrenesulfonate), or poly (3-hexylthiophene).

The conductive polymer may be doped with a first dopant selected from the group consisting of dimethyl sulfoxide (DMSO), ethylene glycol (EG), sorbitol and mixtures thereof. If the conductive polymer is doped with the first dopant, the conductive polymer may secure a high conductivity.

The conductive polymer may also be doped with a second dopant selected from the group consisting of 3-glycidyloxypropyl trimethoxysilane (GOPS), polyvinylpyrrolidone (PVP), polyvinyl alcohol (PVA), and mixtures thereof. If the conductive polymer is doped with the second dopant, the conductive polymer improves a moisture stability such that the conductive polymer can be manufactured through a large area solution process by using spin coating or the like, and can improve a stability for a moisture environment of the human body.

Although a metal nanowire is suitable for a flexible element differently from a general metal, the metal nanowire has a low flexibility compared to the conductive polymer. However, the metal nanowire has a higher conductivity than the conductive polymer, and has much more transparent properties compared to the same resistance criterion.

The metal nanowire may be a nanowire of a metal selected from the group consisting of silver, nickel, copper, aluminum, gold, and alloys thereof.

The metal nanowire may have a length of 10 to 40 μm, and may have a diameter of 20 to 40 nm.

As the electrode sites 120 are formed in a bilayer including the metal nanowire layer 121 disposed on the substrate 110 and the conductive polymer layer 122 disposed on the metal nanowire layer 121, the electrode sites 120 are transparent and flexible, and also can obtain characteristics of excellent brainwave detection performance by having excellent electrical performance and high surface-to-volume ratio.

Meanwhile, the electroconductive contacts 130 receive signals recorded in the electrode sites 120 to amplify, display, store and analyze the received signals, and are electrically connected to an external device.

The electroconductive interconnector 140 may include a circuit 141 for transmitting electrical signals of the electrode sites 120, a circuit 142 for transmitting electrical signals of the electroconductive contacts 130, and a portion in which the circuits 141 and 142 connect to each other.

The electroconductive contacts 130 and the electroconductive interconnector 140 may be formed of a metal material or a carbon material.

The metal material may be one selected from the group consisting of platinum, iridium, tungsten, iron, nickel, copper, zinc, titanium, aluminum, silver, gold, and alloys thereof. The metal material may be a pure metal or an alloy, and may be oxides of metals.

Examples of the metal material may include platinum or platinum-iridium alloy having a low impedance and a high current allowance, tungsten with relatively low distortion in magnetic resonance imaging, a bilayer of gold and titanium, and others.

Examples of a form of the metal material may include various forms such as a metal plate, a multilayer metal film, a spherical metal particle, a metal mesh, a metal gauze, a perforated metal foil, a sintered metal fiber mesh, etc., and it is understood that this is only an example and other exemplary embodiments are not limited to geometrical structures and elemental compositions of the materials.

The carbon material is effective in reducing image distortion due to its low magnetic susceptibility and high transparency. For example, the carbon material may be one selected from the group consisting of graphene, carbon nanotube, carbon nanofiber, fullerene, and expanded graphite.

For example, graphene may be included in the form of a single graphene sheet or two or more graphene sheets. Although the more the number of graphene sheets, the higher electroconductivity of the graphene sheets, but the graphene sheets may reduce transparency. Therefore, a layer number of the graphene sheets existing in a region of the electroconductive interconnector 140 is most preferably 1 to 10 layers.

The graphene sheet may be transparent in a wide wavelength range including wavelengths of ultraviolet (UV) light, visible light and infrared (IR) ray regions of electromagnetic spectrums, and specifically in a wavelength range of 300 to 2,000 nm.

A thermal annealing process or a current annealing process may be performed on the bonded portion to reduce a contact resistance of a bonded portion between electrode sites 120 including the metal nanowire layer 121 and the conductive polymer layer 122 and the electroconductive interconnector 140 formed of a metal material or a carbon material. Although the present disclosure is not limited to the annealing process if the annealing process is a method of changing properties of the metal material and the carbon material by rapidly changing temperatures of the metal material and the carbon material, the annealing process may comprise: treating the metal material and the carbon material with nitric acid and removing impurities from the metal material and the carbon material to obtain an impurity-removed copper foil; annealing the impurity-removed copper foil at 200 to 400° C. by supplying a hydrogen ($H_2$) gas to the impurity-removed copper foil under an argon (Ar) atmosphere and a pressure of 90 to 110 torr to prevent nucleation of the carbon material; and performing an oxidization process on the annealed copper foil at 150 to 300° C. for 5 to 7 hours. As a biocompatible dielectric substrate 110 is sensitive to heat, it is most preferable to perform the annealing process at an annealing temperature of 200 to 400° C.

The substrate 110 may be formed of a transparent biocompatible dielectric material. Here, a biocompatibility means that material is not harmful to a scar of neighboring tissues, does not give a stimulus to the neighboring tissues, or does not deteriorate intended functions in characteristics of a biological tissue that should be transplanted. It is understood that the substrate 110 may be a material which is entirely transparent and biocompatible, but the substrate 110 may include a material which is partially opaque or non-biocompatible as necessary.

Further, as the substrate 110 exhibits mechanical flexibility, the substrate 110 does not cause cracks, divisions, or other damages to a device, and may be consistent with a tissue such as nerve cortex surfaces.

A polymer which can be used as the substrate 110 material may be one selected from the group consisting of parylene (parylene C), polyethylene, polydimethylsiloxane (PDMS), polyester (PET), polyimide (PI), polyethylene naphthalate (PEN), polyetherimide (PEI), and copolymers thereof.

Further, the polymer may be a shape memory polymer, i.e., a polymer which undergoes a deformation from a plane to a non-plane in response to temperature changes. For example, although the shape memory polymer may take a planar structure at room temperature (approximately 23° C.), a nonplanar shape may be adopted at the body temperature of a subject in which a transparent flexible bioelectrode 100 is transplanted.

An example of a dielectric shape memory polymer which is transparent and biocompatible is disclosed in T. Ware, D. Simon, R. L. Rennaker, W. Voit, Smart Polymers for Neural Interfaces, Polymer Reviews 53 (1), 108-129 and Xie T. Recent advances in polymer shape memory. Polym. 2011; 52; 4985-5000. As the contents thereof are associated with a shape memory polymer, the contents are included in the present disclosure by reference.

It is preferable that the substrate 110 has a sufficiently thin thickness to provide a device which is sufficiently transparent and mechanically flexible. Specifically, the substrate 110 has a thickness of 100 μm or less, preferably 50 μm or less, and most preferably 20 μm or less.

The transparent flexible bio-electrode 100 may additionally include an overlayer 150 on the electrode sites 120 and the electroconductive contacts 130. The overlayer 150 protects and isolates the interconnector 140. The overlayer 150 may include opening parts 151 and 152 such that the electrode sites 120 and the electroconductive contacts 130 are exposed and connected to an external device.

As with the substrate 110, the overlayer 150 may also be mechanically flexible and include a dielectric material which is transparent and biocompatible. Although the overlayer 150 may be produced from the same material as the substrate 110, the overlayer 150, for example, may comprise a cyclic olefin polymer represented by the following chemical formula 1:

[Chemical Formula 1]

In chemical formula 1, X and Y are each independently a substituent selected from the group consisting of a hydrogen group, an alkyl group, an alkoxy group, an alkylether group, an aryl group, and combinations thereof, and specifically X or Y may be a substituent derived from diethylene glycol methyl ethyl ether represented by chemical formula 2. And 'n', as the number of repeating units, may be appropriately adjusted according to molecular weight of the cyclic olefin polymer.

[Chemical Formula 2]

The cyclic olefin polymer represented by chemical formula 1 may be a biocompatible material, and may be shaped into a desired pattern by using photoactive properties thereof. Further, the transparent flexible bio-electrode 100 may have a flat overall structure except for portions of the electrode sites 120 by flattening properties of the cyclic olefin polymer.

It is preferable that the overlayer 150 has a sufficiently thin thickness to provide a device which is sufficiently transparent and mechanically flexible. For example, the overlayer 150 may have a thickness of 100 μm or less, preferably 50 μm or less, and most preferably 20 μm or less. Transparency of the transparent flexible bio-electrode 100 reflects a combined transparency of the electrode sites 120, the electroconductive contacts 130, the electroconductive interconnector 140, material of the substrate 110, material of the overlayer 150, and others. The transparency of the transparent flexible bio-electrode 100 includes wavelengths of ultraviolet (UV) light, visible light and infrared (IR) ray regions of electromagnetic spectrums, and specifically in a wavelength range of 300 to 2,000 nm, and preferably 400 to 1,800 nm.

Figure 4:
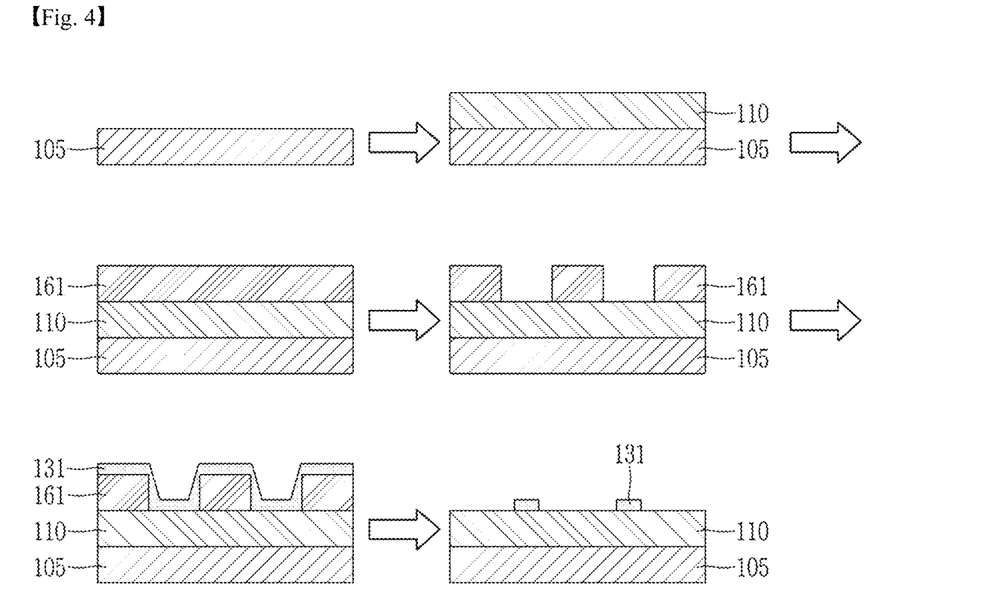
FIGS. 4 to 6 are cross-sectional views of transparent flexible bio-electrodes illustrating a method for manufacturing a transparent flexible bio-electrode according to an exemplary embodiment.
Figure 5:
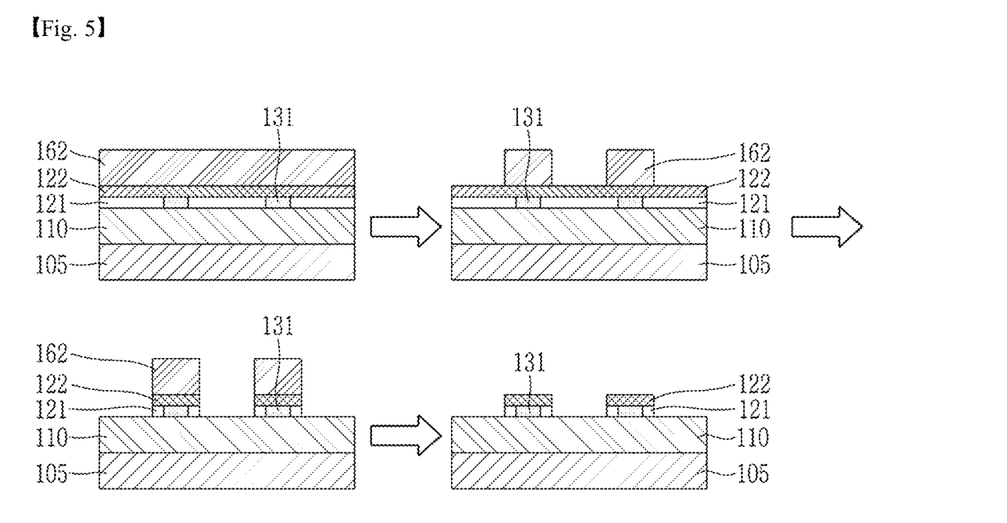
Figure 6:
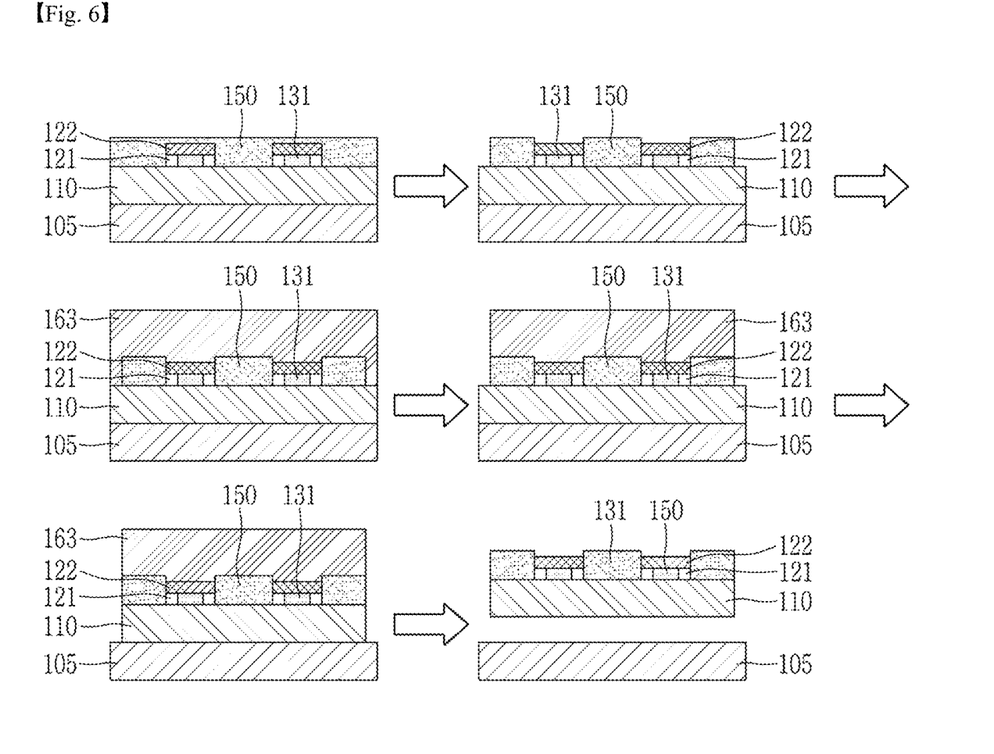

FIGS. 4 to 6 are cross-sectional views of transparent flexible bio-electrodes illustrating a method for manufacturing a transparent flexible bio-electrode.

Referring to FIG. 4, a substrate 110 is formed by coating a substrate forming composition on a cleaned silicon wafer 105.

A first photoresist layer 161 is formed by coating on the substrate 110 a photoresist capable of being used both in a positive tone and a negative tone. The first photoresist layer 161 is patterned through a photolithography. At this time, the first photoresist layer 161 may be formed by using a spin coating.

After depositing metal on the patterned first photoresist layer 161, a metal pattern layer 131 is formed by a lift-off process. The metal pattern layer 131 may be formed of one selected from the group consisting of the electroconductive contacts 130, the electroconductive interconnector 140, and both thereof.

Referring to FIG. 5, a metal nanowire layer 121 and a conductive polymer layer 122 are coated on the substrate 110 including the metal pattern layer 131 formed thereon. Here, FIG. 5 shows a cross-sectional view of a bonded portion between the metal nanowire layer 121 and the electroconductive interconnector 140. In the case of electrode sites 120, except for the bonded portion with the electroconductive interconnector 140, the metal nanowire layer 121 without the metal pattern layer 131 may be directly positioned on the substrate 110.

The metal nanowire layer 121 and the conductive polymer layer 122 may have their front sides easily coated in a large area by using a solution process such as a spin coating or the like.

After coating a second photoresist layer 162 on a bilayer film of the metal nanowire layer 121 and the conductive polymer layer 122, the second photoresist layer 162 is patterned through a photolithography. At this time, the second photoresist layer 162 may be formed by using the spin coating.

The metal nanowire layer 121 and the conductive polymer layer 122 are etched through a reactive ion etching (RIE) by using the second photoresist layer 162 as an etching mask. After performing the etching process, a residual second photoresist layer 162 is removed.

Referring to FIG. 6, an overlayer 150 is formed by coating an overlayer forming material and patterning the coated overlayer forming material by the same process as in the previous layer. Finally, after forming a third photoresist layer 163, the substrate 110 is etched by the reactive ion etching (RIE), and the transparent flexible bio-electrode 100 is released from the silicon wafer 105.

The method for manufacturing a transparent flexible bio-electrode can improve productivity and reduce material consumption by proceeding with a solution process such as spin coating in a wide area of a wafer unit.

Further, the method for manufacturing the transparent flexible bio-electrode has an advantage in mass production using a conductive polymer and a metal nanowire, or inexpensive materials compared to graphene which has been known as conventional transparent neural electrode material.

Hereinafter, one or more exemplary embodiments will be described in detail. However, it is understood that this is only an example and other exemplary embodiments are not limited thereto.

MANUFACTURING EXAMPLES: MANUFACTURING TRANSPARENT FLEXIBLE BIO-ELECTRODES

Example 1: Manufacturing a Transparent Flexible Bio-Electrode Having a PEDOT:PSS/AgNW Electrode First, parylene C was coated on a silicon wafer that had been cleaned by an $N_2$ gun. Parylene C is a material which is transparent and flexible, and biocompatible.

A photoresist AZ5214 which may be used in both a positive tone and a negative tone was coated on parylene C. The coated photoresist was patterned through a photolithography.

After depositing titanium and gold on the patterned photoresist, a metal pattern was formed by a lift-off process using acetone.

Silver nanowire (AgNW) and PEDOT:PSS were spin-coated in a regular sequence on the metal pattern. PEDOT:PSS was used after doping a PH1000 product of Clevious Corporation with dimethyl sulfoxide (DMSO) and 3-glycidyloxypropyl trimethoxysilane (GOPS). DSW-20 of Duksan Hi-metal Co., Ltd was used as the silver nanowire (AgNW).

After spin-coating a photoresist on an AgNW/PEDOT:PSS bilayer film, the photoresist coated on the AgNW/PEDOT:PSS bilayer film was patterned by a photolithography.

An AgNW/PEDOT:PSS bilayer film was etched through a reactive ion etching (RIE) by using the photoresist pattern as an etching mask.

After performing the etching process, a residual photoresist was removed with acetone.

After spin-coating an overlayer material (ZEOCOAT™ ES2110), the overlayer material was patterned by the same process as in the previous layer.

Finally, after etching parylene C by RIE, a microelectrode was released from a wafer.

Comparative Example 1: Manufacturing a Transparent Flexible Bio-Electrode Having a PEDOT:PSS Electrode A transparent flexible bio-electrode was manufactured in the same manner as in Example 1 except that only PEDOT:PSS was spin-coated on the metal pattern without coating the silver nanowire (AgNW) on a metal pattern in Example 1.

Comparative Example 2: Manufacturing a Transparent Flexible Bio-Electrode Having an AgNW Electrode A transparent flexible bio-electrode was manufactured in the same manner as in Example 1 except that only the silver nanowire (AgNW) was spin-coated on the metal pattern without coating PEDOT:PSS on a metal pattern in Example 1.

EXPERIMENTAL EXAMPLES: MEASURING PROPERTIES OF MANUFACTURED TRANSPARENT FLEXIBLE BIO-ELECTRODES

Experimental Example 1: Measuring Resistance and Surface Resistance

Figure 7:
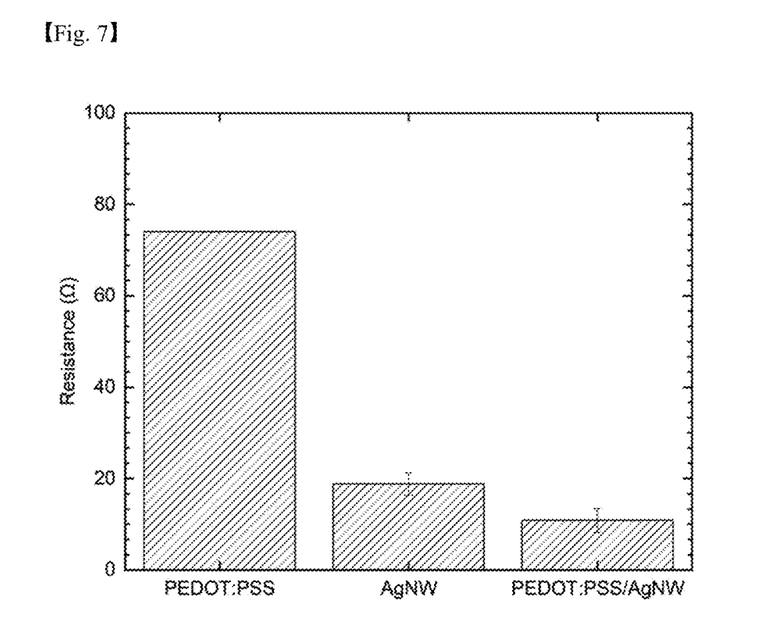
FIGS. 7 and 8 are graphs showing measurement results of measuring resistance and surface resistance values of transparent flexible bio-electrodes manufactured in Example 1, Comparative Example 1 and Comparative Example 2 in Experimental Example 1.
Figure 8:
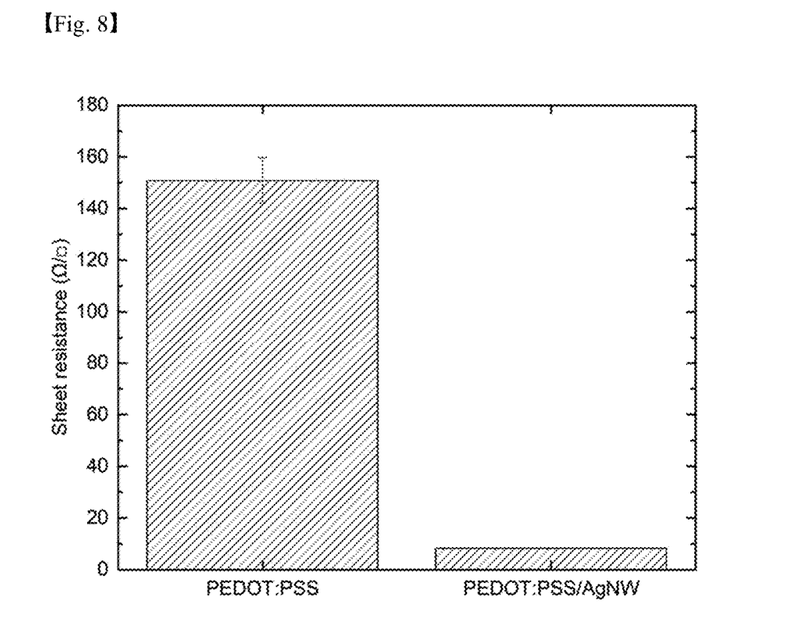

FIGS. 7 and 8 are graphs showing measurement results of measuring resistance and surface resistance values of the transparent flexible bio-electrodes manufactured in Example 1, Comparative Example 1 and Comparative Example 2. However, in FIG. 8, as AgNW is a random network-type film, it is not possible to measure surface resistance values of AgNW. Referring to FIGS. 7 and 8, PEDOT:PSS shows a transparent flexible bio-electrode of Comparative Example 1 including PEDOT:PSS only as the electrode sites, AgNW shows a transparent flexible bio-electrode of Comparative Example 2 including AgNW only as the electrode sites, and PEDOT:PSS/AgNW shows a transparent flexible bio-electrode of Example 1 including a bilayer of PEDOT:PSS and AgNW as the electrode sites.

In the case of the PEDOT:PSS/AgNW sample (i.e., Example 1), after spin-coating AgNW in a rotation speed of 2,000 rpm for 30 seconds, PEDOT:PSS is spin-coated on the coated AgNW in a rotation speed of 2,000 rpm for 30 seconds. The PEDOT:PSS sample (i.e., Comparative Example 1) is measured based on a thickness of 100 nm, and the PEDOT:PSS/AgNW sample (i.e., Example 1) is measured based on a thickness of 150 nm.

Referring to FIGS. 7 and 8, it can be seen that current transferring properties of the transparent flexible bio-electrodes are enhanced by mixing AgNW with PEDOT:PSS, thereby reducing electrical resistance, and the performance of the PEDOT:PSS/AgNW electrode is improved compared to the PEDOT:PSS electrode by reinforcing the current transferring properties of the transparent flexible bio-electrodes.

Experimental Example 2: Measuring Transmittances

Figure 9:
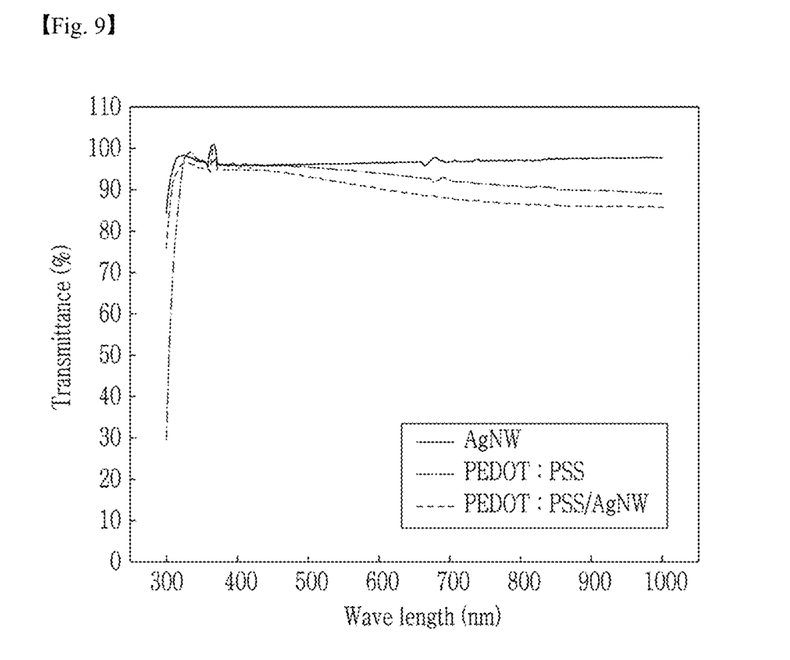
FIG. 9 is a graph showing measurement results of measuring transmittance values of the transparent flexible bio-electrodes manufactured in Example 1, Comparative Example 1 and Comparative Example 2 in Experimental Example 2.

FIG. 9 is a graph showing measurement results of measuring transmittance values in a wavelength range from 300 nm to 1,000 nm with respect to the transparent flexible bio-electrodes manufactured in Example 1, Comparative Example 1, and Comparative Example 2. Referring to FIG. 9, PEDOT:PSS shows a transparent flexible bio-electrode of Comparative Example 1 including PEDOT:PSS only as the electrode sites, AgNW shows a transparent flexible bio-electrode of Comparative Example 2 including AgNW only as the electrode sites, and PEDOT:PSS/AgNW shows a transparent flexible bio-electrode of Example 1 including a bilayer of PEDOT:PSS and AgNW as the electrode sites.

Referring to FIG. 9, it can be seen that, although a total thickness is increased by stacking up two transparent materials, the transparent flexible bio-electrodes still have high transmittance values of 80% or more in ultraviolet light, visible light and infrared ray regions (i.e., a wavelength range of about 300 to 1,000 nm).

Experimental Example 3: Optical Microscope Observation

Figure 10:
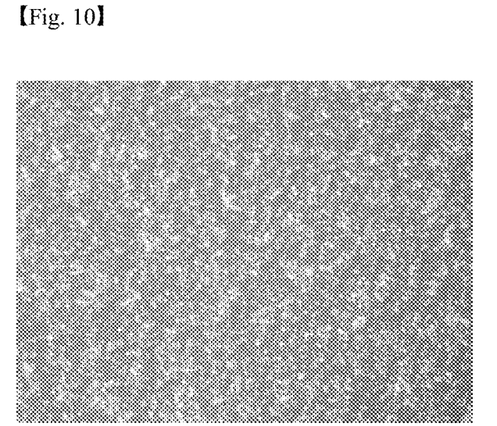
FIGS. 10 and 11 are photographs showing observation results after observing a surface of the transparent flexible bio-electrode manufactured in Example 1 by using an optical microscope in Experimental Example 3.
Figure 11:
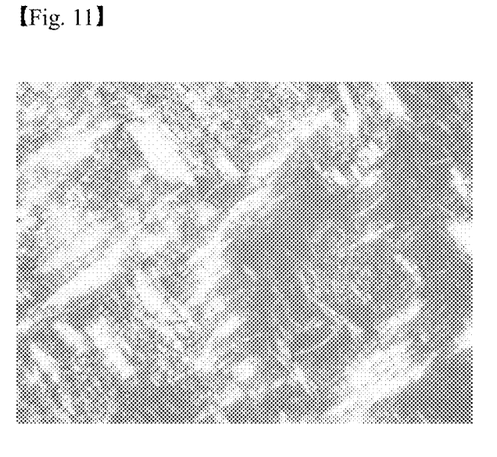

FIGS. 10 and 11 are photographs showing observation results after observing a surface of the transparent flexible bio-electrode manufactured in Example 1 by using an optical microscope. FIG. 10 is a high magnification photograph, and FIG. 11 is a low magnification photograph.

Referring to FIGS. 10 and 11, it can be seen that AgNW random network is entirely covered with PEDOT:PSS, which exists in an empty area free from the random network.

Experimental Example 4: Measuring Surface Roughness Values

Figure 12:
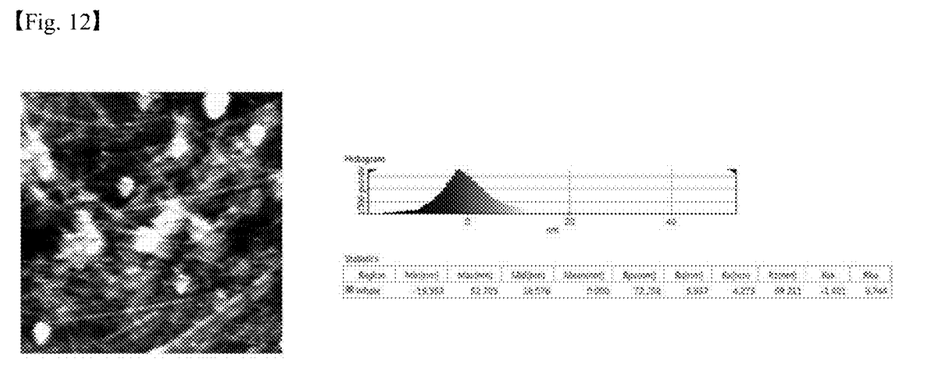
FIGS. 12 and 13 are measurement results of measuring surface roughness values by using atomic force microscopy (AFM) equipment in Experimental Example 4.
Figure 13:
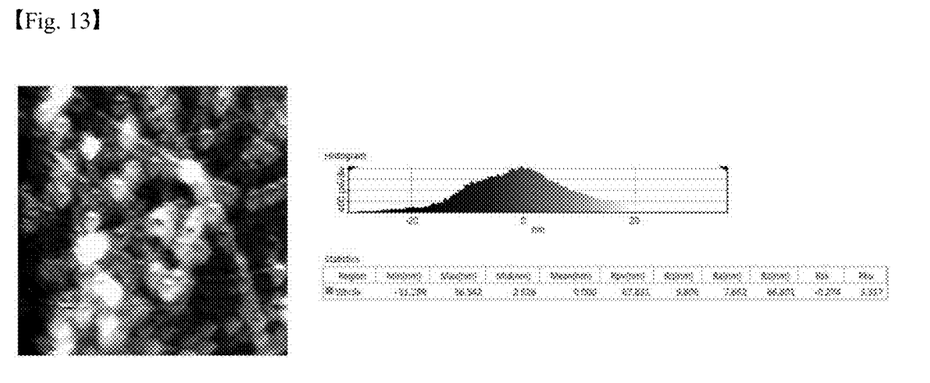

FIGS. 12 and 13 are measurement results of measuring surface roughness values of a conductive polymer layer in the surface of the transparent flexible bio-electrode manufactured in Example 1 by using atomic force microscopy (AFM) equipment.

Here, an average value (Rq) of Z-axis height in the AFM measurement results is an average surface roughness. Assuming that a thickness of PEDOT:PSS is 100 nm, a minimum Z-axis height for AFM measurement is a minimum point of 100 nm thickness. The measurement process was performed in an area of 10×10 μm size. The measurement process was performed twice at set points of 100 nm and 80 nm to increase an accuracy. The set point is a gap between the measuring surface and a tip of the measuring equipment.

FIG. 12 is measurement results when the set point is 100 nm, and FIG. 13 is measurement results when the set point is 80 nm.

Referring to FIG. 12, 0 nm of a histogram is 100+(−min), and an average thickness is 100+(−min)+Rq=125.49 nm. Therefore, a transparent flexible bio-electrode with a thickness range of 100 nm to 172.258 nm is obtained in FIG. 12. Referring to FIG. 13, a transparent flexible bio-electrode with an average thickness value of 141.095 nm and a thickness range of 100 nm to 167.831 nm is obtained.

A transparent flexible bio-electrode according to the exemplary embodiment is transparent and flexible, is formed of biocompatible materials such that the transparent flexible bio-electrode has biocompatibility, and is excellent in brainwave detection performance by having excellent electrical performance and high surface-to-volume ratio.

A method for manufacturing a transparent flexible bio-electrode according to the exemplary embodiment can manufacture a large quantity of a microscale microelectrode to a large area on a wafer by using a solution process, and can reduce costs by improving productivity and adjusting consumption of material.

While exemplary embodiments have been described with reference to the accompanying drawings, it is to be understood by those skilled in the art that various modifications in form and details may be made therein without departing from the sprit and scope as defined by the appended claims. Therefore, the description of the exemplary embodiments should be construed in a descriptive sense and not to limit the scope of the claims, and many alternatives, modifications, and variations will be apparent to those skilled in the art.

What is claimed is:

1. A transparent flexible bio-electrode comprising:
    a substrate;
    electrode sites disposed at one side on the substrate;
    electroconductive contacts disposed at the other side on the substrate; and
    an interconnector configured to connect the electrode sites and the contacts,
    wherein
    the electrode sites comprise a metal nanowire layer disposed on the substrate,
    a conductive polymer layer disposed on the metal nanowire layer,
    the metal nanowire layer comprising a plurality of nanowires, wherein each of the plurality of nanowires having a diameter of 20 to 40 nm, and
    a thickness of the conductive polymer layer is 90 to 200 nm.

2. The transparent flexible bio-electrode of claim 1, wherein the conductive polymer layer has irregularities depending on whether the plurality of nanowires exist under the conductive polymer layer.

3. The transparent flexible bio-electrode of claim 2, wherein a ratio (ratio 2/ratio 1) of a surface area to a volume is 1.5 to 2.0, the ratio 2 being a ratio of a surface area to a volume when the metal nanowire layer is formed on the substrate and the conductive polymer layer is formed on the metal nanowire layer, and the ratio 1 being a ratio of a surface area to a volume when only the conductive polymer layer is formed on the substrate.

4. The transparent flexible bio-electrode of claim 1, wherein a thickness of the electrode sites is about 100 to 173 nm.

5. The transparent flexible bio-electrode of claim 1 wherein the conductive polymer layer is one selected from the group consisting of poly (3, 4-ethylenedioxythiophene) (PEDOT), poly (styrenesulfonate) (PSS), poly (3-hexylthiophene) (P3HT), poly (3-octylthiophene) (P3OT), poly (p-phenylene vinylene) (PPV), poly (9, 9-dioctylfluorene), poly (2-methoxy-5-(2'-ethyl-hexyloxy)-1, 4-phenylene vinylene) (MEH-PPV), poly (2-methoxy-5-(3', 7'-dimethyloctyloxy)-1, 4-phenylenevinylene) (MDMO-PPV), derivatives thereof, and mixtures thereof.

6. The transparent flexible bio-electrode of claim 1 wherein the conductive polymer layer is doped with a first dopant selected from the group consisting of dimethyl sulfoxide (DMSO), ethylene glycol (EG), sorbitol and mixtures thereof, and a second dopant selected from the group consisting of 3-glycidyloxypropyl trimethoxysilane (GOPS), polyvinylpyrrolidone (PVP), polyvinyl alcohol (PVA), and mixtures thereof.

7. The transparent flexible bio-electrode of claim 1 wherein the plurality of nanowires is a metal selected from the group consisting of silver, nickel, copper, aluminum, gold, and alloys thereof.

8. The transparent flexible bio-electrode of claim 1, wherein the transparent flexible bio-electrode further comprises an overlayer comprising a cyclic olefin polymer represented by following Chemical Formula 1 on the electrode sites and the electroconductive contacts,

[Chemical Formula 1]

where, X and Y are each independently a substituent selected from the group consisting of a hydrogen group, an alkyl group, an alkoxy group, an alkylether group, an aryl group, and combinations thereof, and n is a number of repeating units.

9. The transparent flexible bio-electrode of claim 8, wherein the overlayer comprises opening parts such that the electrode sites and the electroconductive contacts are partially exposed and connected to an external device.

10. The transparent flexible bio-electrode of claim 8, wherein a thickness of the overlayer is 50 μm or less.

11. The transparent flexible bio-electrode of claim 1, wherein a thickness of the substrate is 50 μm or less.

* * * * *